(12) United States Patent
Hamersky et al.

(10) Patent No.: US 7,459,494 B2
(45) Date of Patent: *Dec. 2, 2008

(54) PHASE CHANGE SOLVENTS FOR THERMOPLASTIC ELASTOMERS

(75) Inventors: Mark William Hamersky, Hamilton, OH (US); Steven Daryl Smith, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/429,432

(22) Filed: May 5, 2003

(65) Prior Publication Data

US 2004/0024109 A1 Feb. 5, 2004

Related U.S. Application Data

(60) Provisional application No. 60/400,282, filed on Jul. 31, 2002.

(51) Int. Cl.
*C08K 5/00* (2006.01)

(52) U.S. Cl. .................. 524/219; 524/239; 524/294; 524/296; 524/297; 524/298

(58) Field of Classification Search .......... 524/296, 524/297, 298, 219, 239, 294; 560/76; 528/308.7
See application file for complete search history.

(56) References Cited

U.S. PATENT DOCUMENTS

| | | |
|---|---|---|
| 2,075,107 A | 3/1937 | Frazier |
| 3,562,356 A | 2/1971 | Nyberg et al. |
| 3,734,891 A | 5/1973 | Knopka |
| 3,755,231 A | 8/1973 | Muir et al. |
| 3,981,838 A * | 9/1976 | Wilson .............. 524/295 |
| 4,131,581 A | 12/1978 | Coker |
| 4,293,473 A | 10/1981 | Eastman |
| 4,387,214 A | 6/1983 | Passmore et al. |
| 4,442,270 A | 4/1984 | Passmore et al. |
| 4,578,302 A | 3/1986 | Schmidt, Jr. et al. |
| 4,618,630 A * | 10/1986 | Knobel et al. ........... 521/105 |
| 4,704,110 A | 11/1987 | Raykovitz et al. |
| 4,745,026 A | 5/1988 | Tsukahara et al. |
| 4,882,375 A | 11/1989 | Tyrell et al. |
| 5,352,531 A | 10/1994 | Roberts et al. |
| 5,389,711 A | 2/1995 | Westbrook et al. |
| 5,418,281 A | 5/1995 | Yung et al. |
| 5,503,919 A | 4/1996 | Litchholt et al. |
| 5,534,303 A | 7/1996 | Roberts et al. |
| 5,534,583 A | 7/1996 | Roberts et al. |
| 5,540,983 A | 7/1996 | Maris et al. |
| 5,624,986 A | 4/1997 | Bunnelle et al. |
| 5,627,229 A | 5/1997 | Bunnelle et al. |
| 5,633,319 A | 5/1997 | Silvi et al. |
| 5,714,254 A | 2/1998 | Jacob |
| 5,853,874 A | 12/1998 | Jacob |
| 5,895,718 A * | 4/1999 | Ishimura et al. ............ 525/437 |
| 5,910,527 A | 6/1999 | Alper et al. |
| 5,939,483 A | 8/1999 | Kueppers |
| 5,945,485 A | 8/1999 | Struglinski et al. |
| 6,080,480 A | 6/2000 | Shiba et al. |
| 6,117,176 A | 9/2000 | Chen |
| 6,177,508 B1 | 1/2001 | Ohmori et al. |
| 6,187,425 B1 | 2/2001 | Bell et al. |
| 6,344,515 B1 | 2/2002 | Parikh |
| 6,703,115 B2 | 3/2004 | Hale et al. |
| 6,723,444 B2 | 4/2004 | Kobayashi et al. |
| 7,241,837 B2 | 7/2007 | Yaguchi |

FOREIGN PATENT DOCUMENTS

| | | |
|---|---|---|
| EP | 0 044 675 B1 | 5/1984 |
| EP | 0 277 750 | 8/1988 |
| EP | 0 989 162 A1 | 3/2000 |
| EP | 1 193 284 A1 | 4/2002 |
| GB | 849086 | 9/1960 |
| GB | 1181807 | 2/1970 |
| GB | 1190417 | 5/1970 |
| GB | 1193626 | 6/1970 |

(Continued)

OTHER PUBLICATIONS

Chem. Abstracts 1996:310113, "End-grafting oligoesters based on terephthalic acid and linear diols for high solids coating", Teng et al., Journal of Applied Polymer Science (1996) 60(10), 1609-1618.

(Continued)

*Primary Examiner*—Peter D Mulcahy
(74) *Attorney, Agent, or Firm*—Dara M. Kendall; Richard L. Alexander; Julie A. McConihay

(57) ABSTRACT

Novel elastomeric compositions that contain at least one thermoplastic elastomer and at least one phase change solvent. Above the phase change temperature, the phase change solvent solubilizes or intimately mixes with the thermoplastic elastomers. Below the phase change temperature, the phase change solvent solidifies or crystallizes within the thermoplastic matrix. The phase change behavior of these materials produce elastomeric compositions that exhibit lowered viscosity and lowered processing temperature without substantially compromising the mechanical properties. The present invention also relates a method of lowering the viscosity and improving the processability of a thermoplastic elastomer using the phase change solvent.

24 Claims, 3 Drawing Sheets

| | FOREIGN PATENT DOCUMENTS | |
|---|---|---|
| GB | 1193627 | 6/1970 |
| JP | 63-069850 A | 3/1988 |
| JP | 2189348 A2 | 7/1990 |
| JP | 02196844 | 8/1990 |
| JP | 05125240 | 5/1993 |
| JP | 08-073695 A | 3/1996 |
| JP | 11-349704 A | 12/1999 |
| WO | WO 96/05253 A1 | 2/1996 |
| WO | WO 00/11092 | 3/2000 |

OTHER PUBLICATIONS

Chem. Abstracts 1992:21832, "Liquid-crystalline oligoesters containing single-ringaromatic units separated by aliphatic spacers", Teng et al., Polymeric Materials Science and Engineering (1991), 65, 33-4.

Chem. Abstracts 1995:976847, "A test of the applicability of small-molecule group additivity parameters in the estimation of fusion entropies of macromolecules", Chickos et al., Thermochimica Acta (1995), 264, 13-26.

* cited by examiner

PHASE CHANGE SOLVENTS FOR THERMOPLASTIC ELASTOMERS

CROSS REFERENCE TO RELATED APPLICATION

This application claims the benefit of U.S. Provisional Application No. 60/400,282, filed Jul. 31, 2002.

FIELD OF INVENTION

The present invention relates to novel elastomeric compositions containing phase change solvents. Above the phase change temperature, the phase change solvents solubilize or intimately mix with the thermoplastic elastomers. Below the phase change temperature, the phase change solvents solidify or crystallize within the thermoplastic elastomer matrix. The phase change behavior of these agents produce elastomeric compositions that exhibit lowered viscosity and lowered processing temperature without substantially compromising the mechanical properties. The present invention also relates a method of lowering the viscosity and improving the processability of a thermoplastic elastomer using the phase change solvent.

BACKGROUND

Block copolymers comprising one or more alkenylarene polymer block and one or more olefinic polymer block are generally known as thermoplastic elastomers (TPE's). The block copolymers are elastomeric in the sense that they typically have a three-dimensional, entangled (alternatively known as "physically crosslinked") structure below the glass transition temperature ($T_g$) of the stryenic block such that they exhibit elastic memories in response to external forces. The block copolymers are thermoplastic in the sense that they can be softened or melted above the glass or crystalline transition temperature of the alkenylarene block, processed, and cooled/solidified several times with little or no change in physical properties (assuming a minimum of oxidative degradation).

These block copolymers are known to have high strength and elasticity at ambient temperatures. The high strength and elasticity of these block copolymers are due to the microphase separated network structure wherein the olefinic blocks and the alkenylarene blocks separate from structurally dissimilar blocks and entangle with structurally similar blocks to form separate domains. The olefinic blocks typically have a glass transition temperature below ambient temperature, thus, they are relatively free to move about and form the soft, rubbery phase at or above ambient temperature. In contrast, the alkenylarene blocks have a glass and/or crystalline transition temperature above ambient temperature, thus, they are relatively immobilized in the entangled state and form the hard phase. However, at body temperature, the copolymers may begin to lose their mechanical properties after some time. The deterioration of properties appears to be associated with the copolymer movements, especially the movements of the alkenylarene blocks. At body temperature, sometimes accompanied with tension or load, the previously immobile alkenylarene blocks begin to slip pass neighboring alkenylarene blocks. Since the alkenylarene blocks form the hard phases, which are primarily responsible for the mechanical properties, such motions of the alkenylarene blocks adversely effect the mechanical properties of the copolymer.

Plasticizers or processing oils are often added to the block copolymers to lower the viscosity and improve the processability of the block copolymers. Other polymers may also be added to compatibilize the blends and/or improve the mechanical properties. Blends comprising block copolymers are described in U.S. Pat. Nos. 3,562,356 (Nyberg et al.); U.S. Pat. No. 4,704,110 (Raykovitz et al.); U.S. Pat. No. 4,578,302 (Schmidt et al.); U.S. Pat. No. 5,503,919 (Litchholt, et al.); U.S. Pat. No. 5,540,983 (Maris et al.); U.S. Pat. No. 6,117,176 (Chen); and U.S. Pat. No. 6,187,425 (Bell et al.).

However, the addition of the plasticizers and/or processing oils lower the strength and elastic properties of the block copolymer compositions.

Therefore, it is desirable to provide a novel material that lowers the viscosity and improves the processability of block copolymer compositions without substantially compromising their mechanical properties.

It is also desirable to provide a novel material that exhibits a phase change as the temperature is raised and/or lowered such that the novel material effects very sharp changes in the characteristics (e.g., viscosity) of the block copolymer compositions at or around the phase change temperature of the novel material.

It is further desirable that the phase change temperature of the novel material can be controlled by its molecular characteristics, such as the monomeric structure, the molecular weight, the aromatic and aliphatic carbon content in the backbone, and the like.

Moreover, it is desirable that the viscosity of the phase change solvent and of its block copolymer blends can be varied over a broad range to achieve the suitable viscosity for different fabricating processes, such as extrusion, injection molding, melt spinning, blow molding, spraying, printing, coating, and the like.

SUMMARY OF THE INVENTION

The present invention relates to novel elastomeric composition containing phase change solvents. The compositions may comprise:

a) a thermoplastic elastomer which is a block copolymer having at least one soft block and at least one hard block;

b) a phase change solvent having the general formula:

$$R'-P_y-(Q-P_x)_{n-1}-Q-P_y-R; \quad (I)$$

$$R'-P_y-(Q-P_x)_n-R; \quad (II)$$

$$R'-(Q-P_x)_n-R; \quad (III)$$

$$R'-(Q-P_x)_{n-1}-Q-P_y-R; \quad (IV)$$

$$R'-(Q-P_x)_{n-1}-Q-R; \text{ or} \quad (V)$$

mixtures thereof, (VI)

wherein Q may be a substituted or unsubstituted difunctional aromatic moiety; P is $CH_2$; R and R' are the same or different and are independently selected from H, $CH_3$, COOH, $CONHR_1$, $CONR_1R_2$, $NHR_3$, $NR_3R_4$, hydroxy, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 1 to 7;

c) optionally, a processing oil;

d) optionally, a nucleating agent; and e) optionally, a thermoplastic polymer.

Typically, the phase change solvent has a phase change in a temperature range from about 40° C. to about 250° C. The resulting compositions exhibit low viscosities, low processing temperatures and good mechanical properties. The elastomeric composition may be processed by various methods, including extrusion, injection molding, melt spinning, blow molding, printing, spraying, coating, and the like.

The present invention also relates a method of lowering the viscosity and improving the processability of a thermoplastic elastomer using the phase change solvent.

All documents cited are, in relevant part, incorporated herein by reference; the citation of any document is not to be construed as an admission that it is prior art with respect to the present invention.

DETAILED DESCRIPTION OF THE INVENTION

Figure 1:
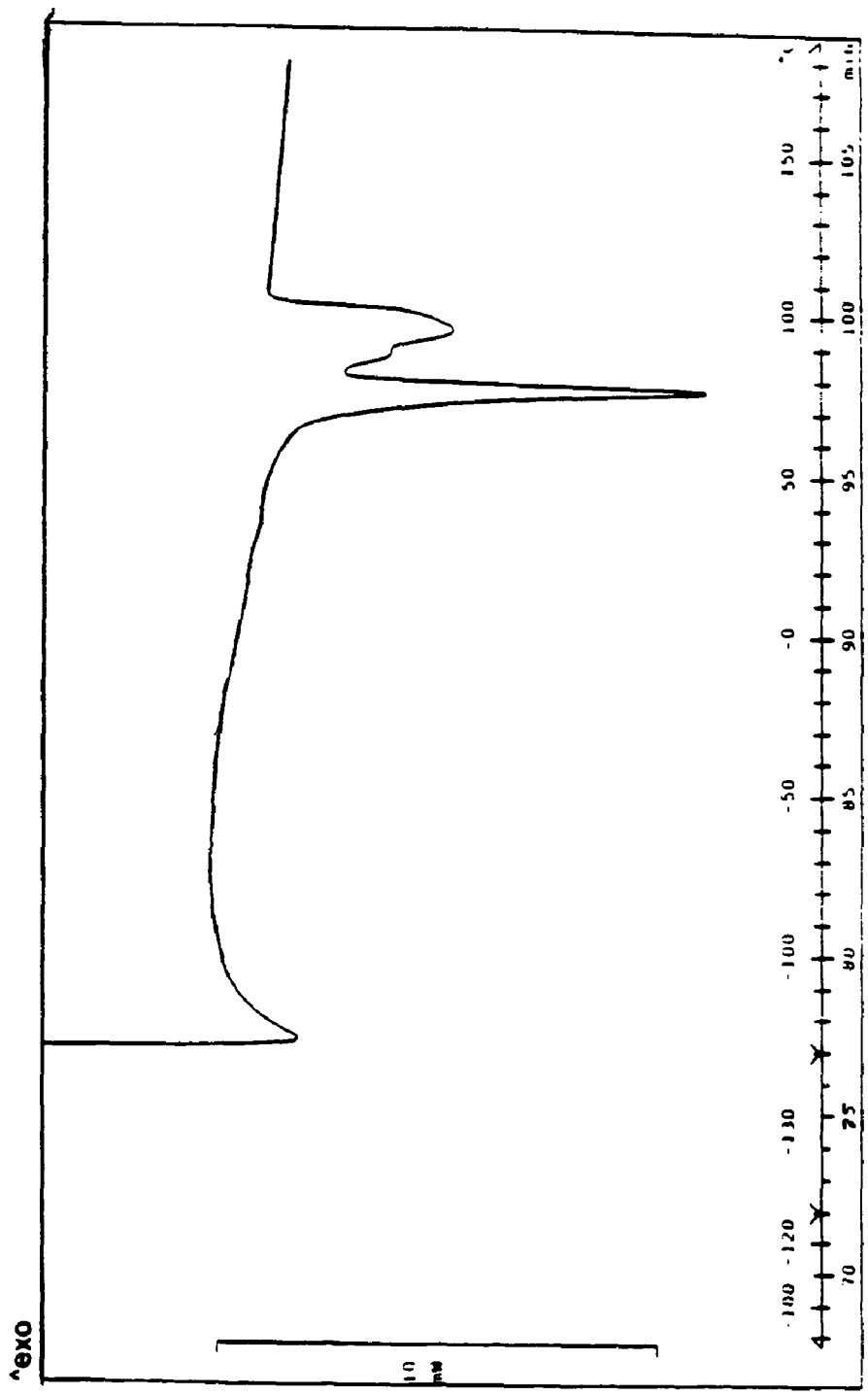
FIG. 1 is a DSC thermogram showing the phase change properties of a phase change solvent of the present invention.

As used herein, the terms "elastic" or "elastomeric" refer to any material which is capable of being elongated or deformed to at least 200% of its original dimension under an externally applied force, and which will substantially resume its original dimension, sustaining only small permanent set (typically no more than about 20%), after the external force is released. The term "elastomer" refers to any material exhibiting elastic properties as described hereinabove.

As used herein, the term "thermoplastic" refers to any material that can be melted and re-solidified with little or no change in physical properties (assuming a minimum of oxidative degradation).

As used herein, the term "AA ratio" refers to ratio between the number of aliphatic carbons in the P units to the number of aromatic carbons in the Q units of the phase change solvent, wherein the aromatic carbons of the Q units exclude those carbons that may be present in the substituents.

As used herein, the term "percent elongation" refers to the ratio obtained from dividing the length of the sample material measured at a specific condition (e.g., while the sample material is elongated under an applied force) by the length of the sample material in its undeformed state, then multiplied by 100. Thus, a sample material in its undeformed or unstrained state has a 100% elongation.

As used herein, the term "percent strain" refers to the difference between the length of the sample material measured at a certain elongation and the length of the samples material in its undeformed state, divided by the length of the sample material in its undeformed state, then multiplied by 100. Thus, a sample material in its undeformed or unstrained state has a 0% strain.

As used herein, the term "stress relaxation" or "force relaxation" refers to the percentage loss of load (i.e., tension force) between the maximum load encountered after elongating a sample material at a specific rate of strain to a predetermined length and the remaining load measured after the sample material has been held at that length for a specified period of time. Stress relaxation is expressed as percentage loss of the initial load after a specific period of time at a specific strain of a sample material.

As used herein, the term "comprising" means that the various components, ingredient, or steps can be conjointly employed in practicing the present invention. Accordingly, the term "comprising" encompasses the more restrictive terms "consisting of" and "consisting essentially of".

Other terms are defined herein where initially discussed.

All percentages, ratios and proportions used herein are defined by weight of the composition unless otherwise specified.

The phase change solvent may be a low molecular weight resin or oligomer having one or more low phase change temperatures. Further, the phase change solvent may have a chemical structure that is sufficiently similar to the chemical structure of some TPE's, such as styrenic TPE's, so that the phase change solvent may be intimately mixed with the TPE's. The phase change solvent, when blended with TPE's, may achieve more flexible processing conditions and over a broader processing temperature range. The phase change solvent may also improve the mechanical properties, such as tensile and elastic properties, of the elastomeric compositions in the temperature range below its phase transition temperature.

The phase change solvent may change the viscosity of the elastomeric composition. In the range of its phase change temperature, the phase change solvent may effect a rapid change in viscosity of the elastomeric composition. This rapid change in viscosity may render the elastomeric composition processable at a temperature much lower than the typical melt processing temperature of the TPEs that is typically about 190° C. or higher. Because of the lower processing temperature, substrates with lower thermal stability (e.g., polyethylene and the like) and or delicate structures (e.g., nonwoven webs and the like) may be used.

Moreover, the phase change solvents may be used as viscosity modifiers in elastomeric compositions to achieve a wide range of viscosities so that the elastomeric compositions may be suitable for various processes. Elastomeric compositions are previously considered not suitable for processes that operate at low viscosity and/or low temperature, such as gravure printing, flexographic printing, ink jet printing, spraying, coating and the like, because they typically have high viscosities at the processing temperature of the equipment. Volatile solvents and/or high temperature may be used to reduce the viscosity of the elastomeric compositions. The present invention uniquely provides "solvent-less" (i.e., no volatile solvents) elastomeric compositions that may be useful in these processes at an operable processing temperature of the equipment.

Traditional extrusion processes produce sheets or strands of elastomeric materials. Subsequent cutting of the elastomeric sheets or stands to the desired size and/or shape and joining the cut pieces to a substrate are typically required. Overall, the above processes involve multiple steps to produce the finished product and generate a lot of wasted materials. In view of these drawbacks, the ability to print or spray elastomeric compositions is particularly advantageous. The printing and spraying processes may deliver the elastomeric materials directly onto the substrate, thus, avoiding the drawback of a multi-step process. These processes may also deliver the elastomeric materials only to targeted areas where elastic properties are needed, thus, minimizing the amount of waste generated. Moreover, these processes may also provide controlled delivery of varying amounts of elastomeric materials to discrete areas in a single step, which is difficult, if not impossible to achieve by traditional extrusion/molding processes.

Other processes, such as fiber spinning, melt blowing, require low melt viscosity materials, which are typically thermoplastic polymers such as polyethylene, polypropylene, polyesters, polyamides. Elastomeric materials having suitably low melt viscosity for these processes are olefinic elastomers made from single site catalysts. Styrenic block copolymer compositions are generally considered not suitable for such low viscosity processes. Elastomeric compositions of the present invention are uniquely suitable for these low melt viscosity processes.

Further, the phase change solvent uniquely modifies the viscosity without substantially compromising the mechanical properties of the elastomeric compositions. It is well known that plasticizers, viscosity modifiers and processing oils may be used to lower the viscosity and improve the melt processability of TPE's or mixtures thereof. However, due to their low molecular weight and their softness and/or fluidity down to room temperature, these agents tend to reduce the mechanical properties of the TPE's and blends. In contrast, the phase change solvents are solid-like at or below body temperature. Thus, they may function like reinforcing particles (i.e., fillers) in the TPEs and blends. Moreover, the phase change solvents, due to their chemical formula and molecular weights, may be intimately mixed the TPEs and function like compatibilizers. When they solidify, they may be fairly homogeneously dispersed throughout the TPE matrix. Homogeneous distribution of reinforcing particles are desirable since few stress concentration spots (detrimental to mechanical properties) are created in such structures. Their compatibilizing function may also lead to reduced phase sizes and reduced stress concentrations at the interfaces between the phases of the TPE's.

The phase change solvents of the present invention may comprise one or more aliphatic segments having aliphatic carbons in the chain backbone and one or more mixed segments having aromatic carbons dispersed along the aliphatic chain backbone. The phase change solvents may have the following formula:

$$R'-P_y-(Q-P_x)_{n-1}-Q-P_y-R; \quad (I)$$

$$R'-P_y-(Q-P_x)_n-R; \quad (II)$$

$$R'-(Q-P_x)_n-R; \quad (III)$$

$$R'-(Q-P_x)_{n-1}-Q-P_y-R; \quad (IV)$$

$$R'-(Q-P_x)_{n-1}-Q-R; \text{ or} \quad (V)$$

$$\text{mixtures thereof;} \quad (VI)$$

wherein Q is a substituted or unsubstituted difunctional aromatic moiety; P is $CH_2$; the same or different and are independently selected from H, $CH_3$, COOH, $CONHR_1$, $CONR_1R_2$, $NHR_3$, $NR_3R_4$, hydroxy, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 1 to 7.

The Q moieties in a phase change solvent may include terephthalic, naphthalic, phenolic, phenyl or biphenyl having the following formula:

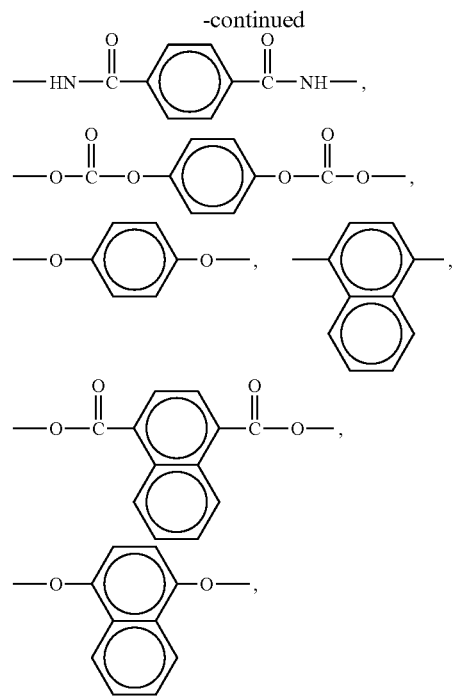

and the like, and mixtures thereof;

Q may be substituted on the aromatic ring with one or more substituents selected from H, C1-C30 alkyl, COOH, $CONHR_5$, $CONR_5R_6$, $NHR_7$, $NR_7R_8$, hydroxy, C1-C30 alkoxy, $SO_3H$, or halogen; wherein $R_5$, $R_6$, $R_7$ and $R_8$ are the same or different and are independently selected from H or linear or branched alkyl from C1-C30.

The phase change solvent may have at least one phase change temperature in the range from about 40° C. to about 250° C., preferably from about 50° C. to about 180° C., more preferably from about 60° C. to about 150° C. The phase change may be a crystalline transition (a first order transition), a glassy transition (a second order transition) or a liquid crystalline transition. A phase change solvent may have one or more phase changes. The definitions of these phase changes can be found in *Principles of Polymer Chemistry*, by Flory, Cornell University Press (1953) and *Liquid Crystals*, by Chandrasekhar Cambridge University Press, 1992. The phase changes may be characterized by standard techniques, such as Differential Scanning Calorimetry (DSC), Differential Thermal Analysis (DTA), and the like.

FIG. 1 a DSC thermogram illustrating the phase changes of the phase change solvent of Example 1. The phase change solvent exhibits multiple first order transitions (shown here as endothermic peaks) in the range from about 60° C. to about 100° C., indicating that this phase change solvent readily crystallizes at or below about 100° C.

Molecular weight of the phase change solvent is a factor to consider. Higher molecular weight materials typically exhibit higher phase change temperatures, which may not effectively lower the processing temperatures and/or viscosities of the elastomeric compositions. Moreover, higher molecular weight materials may not be effective in solubilizing the TPE's, that is, they may not mix intimately with the TPE's. Low molecular weight materials, when blended with TPE's, may function more like traditional plasticizers, processing oils, or other viscosity additives. That is, they may lower the mechanical properties of the resulting elastomeric compositions. Typically, the phase change solvents of the present invention may have a number-average molecular weight from about 150 to about 5000, preferably from about 500 to about 3000, and more preferably from about 800 to about 2500.

The effectiveness of the phase change solvent having formula (I)-(V) may be related to the AA ratio, which is defined as follows:

$$AA\ ratio = C_{aliphatic}/C_{aromatic}$$

wherein $C_{aliphatic}$ is the number of aliphatic carbon (excluding those aliphatic carbons that may be present in the substituents) of the P units of the formula, and $C_{aromatic}$ is the number of aromatic carbons (excluding any aromatic carbons that may be present in the substituents) in the Q units of the formula. For example, formula (I) would have:

$$C_{aliphatic} = 2*y + (n-1)*x$$

and $$C_{aromatic} = n*6\ (\text{if the Q unit is terephthalic, phenolic or phenyl}),$$

or $$C_{aromatic} = n*10\ (\text{if the Q unit is naphthalic or biphenyl}).$$

A typical phase change solvent may have an AA ratio from about 0.25 to about 4, preferably from about 1.0 to about 3.5, more preferably from about 1.5 to 2.7, and most preferably from about 2.0 to about 2.6. Moreover, in some embodiments, the AA ratio of the phase change solvent may be substantially the same as that of the TPE in the compositions. It is found that compositions containing phase change solvent and TPE with similar AA ratios exhibit lower viscosity. The difference in AA ratio between the phase change solvent and TPE may have an absolute value of less than about 1.5, preferably less than about 1, and more preferably less than about 0.5.

The phase change solvent may be present in the elastomeric composition in an amount from about 1 to about 70 weight percent, preferably from about 10 to about 60 weight percent, and more preferably from about 20 to about 50 weight percent, of the composition.

Block copolymers suitable for use herein may comprise one "hard" polymeric block and one "soft" polymeric block. Typically, the hard blocks (or the A blocks) are either amorphous and have a second order transition temperature or glass transition temperature above room temperature, or crystalline with a crystallizable segment (which may be in the backbone, in the side chain, or in the pendant groups) and have a first order transition temperature or crystalline melting temperature above room temperature. The soft blocks (or the B blocks) typically have a glass transition temperature below room temperature. The soft blocks are relatively mobile at room temperature. The hard blocks and the soft blocks tend to segregate from one another and form separate domains. These copolymers are generally referred to as thermoplastic elastomers (TPE's), wherein the hard A blocks exhibit substantially thermoplastic characteristic, and the soft B blocks exhibit substantially elastomeric characteristic.

The hard block may comprise a polyalkenylarene derived from monomers such as styrene, α-methyl styrene, para-methyl styrene, other alkyl styrene derivatives, or mixtures thereof. The hard block may also be a copolymer derived from alkenylarene monomers and short C2-C6 alkene monomers such as ethylenes, propylenes, butylenes; C2-C6 diene monomers such as isoprenes, butadienes; or mixtures of alkene/diene monomers.

The hard block desirably has a number-average molecular weight between from about 1,000 to about 200,000, preferably from about 2,000 to about 100,000, more preferably from about 5,000 to about 60,000. The hard block may comprise from about 10% to about 80%, preferably from about 20% to about 50%, more preferably from about 25 to about 35% of the total weight of the block copolymer.

The soft block may be a diene polymer derived from unsaturated or partially saturated, diene monomers of from about 4 to about 6 carbons. Suitable diene monomers may include butadiene, isoprene, and the like. The soft block may also be an olefinic polymer derived from linear or branched alkene monomers of from about 2 to about 6 carbon atoms. Suitable alkene monomers may include ethylene, propylene, butylene, and the like. The soft block may also comprise a combination of the above monomers, such as ethylene/propylene polymers, ethylene/butylene polymers, and the like.

The number-average molecular weight of the soft block may be from about 1,000 to about 300,000, preferably from about 10,000 to about 200,000, and more preferably from about 20,000 to about 100,000. The soft block may comprise from about 20% to about 90%, preferably from about 50% to about 80%, more preferably from about 65% to about 75% of the total weight of the copolymer.

Block copolymers suitable for use herein may comprise at least one soft, substantially elastomeric block (hereinafter referred to as the "B block") and at least one hard, substantially thermoplastic block (hereinafter referred to as the "A block"). The block copolymers may have multiple blocks, such as A-B-A triblock copolymers, A-B-A-B tetrablock copolymers, or A-B-A-B-A pentablock copolymers, and the like.

Also useful in the present invention are block copolymers having more than one A block and/or more than one B block, wherein each A block may be derived from the same or different alkenylarene monomers and each B block may be derived from the same or different diene or alkene monomers. For example, a triblock copolymer may have an elastomeric midblock B and thermoplastic endblocks A and A', wherein A and A' may be derived from different alkenylarene monomers. The block copolymers may also be radial, having three or more arms, each arm being an B-A, B-A-B-A, or the like type copolymer, the B blocks being at or near the center portion of the radial polymer.

In some embodiments, the olefinic block may comprise at least about 50 percent by weight of the block copolymer. The unsaturation in diene monomer may be selectively hydrogenated, if desired, to reduce sensitivity to oxidative degradation and may result in improved elastic and mechanical properties. For example, a polyisoprene block can be selectively reduced to form an ethylene-propylene block. In other embodiments, the alkenylarene block may comprise at least about 10 percent by weight of the block copolymer. Higher alkenylarene content provides low stress relaxation and high elastic/tensile properties.

Exemplary block copolymers may include styrene-alkene/diene-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprenelbutadiene-styrene (S-IB-S), and mixtures thereof. Commercially available block copolymers include KRATON® from the Shell Chemical Company, Houston, Tex.;

SEPTON® from Kuraray America, Inc. New York, N.Y.; and VECTOR® from Dexco Chemical Company, Houston, Tex.

The block copolymer may be used in the elastomeric composition in an amount effective to achieve the desired mechanical properties, such as tensile, elastic and stress relaxation properties. The block copolymer may be present in the elastomeric composition in an amount from about 1 to about 99 weight percent, preferably from about 20 to about 80 weight percent, and more preferably from about 30 to about 70 weight percent, of the composition.

Optionally, various processing oils may also be used in the present compositions in the amount from about 1 to about 70 wt %, preferably from about 5 to about 60 wt %, more preferably from about 10 to about 50 wt %, and most preferably from about 20 to about 40 wt %. They include the usual processing oil, such as mineral oil, as well as other petroleum-derived oils and waxes, such as parafinic oil, naphthenic oil, petrolateum, microcrystalline wax, paraffin or isoparaffin wax. Synthetic waxes, such as Fischer-Tropsch wax; natural waxes, such as spermaceti, carnauba, ozokerite, beeswax, candelilla, paraffin, ceresin, esparto, ouricuri, rezowax, and other known mined and mineral waxes, are also suitable for use herein. Olefinic or diene oligomers and low molecular weight polymers may also be used herein. The oligomers may be polypropylenes, polybutylenes, hydrogenated isoprenes, hydrogenated butadienes, or the like having a weight average molecular weight between about 350 to about 8000.

Optionally, various nucleating agents may be used in the present compositions. The nucleating agent may induce phase change of the phase change solvent. The nucleating agent may also increase the crystallization or solidification rate of the phase change solvent and/or the composition. The nucleating agents may be inorganic or polymeric.

The inorganic nucleating agent may be inert particulates such as talc, silica, carbon black, clay, metal oxides (e.g., $TiO_2$), metal carbonates (e.g., $CaCO_3$), and mixtures thereof. In some embodiments, the inorganic nucleating agent may be incorporated in the amount from about 0.1 to about 2 wt %.

The polymeric nucleating agents may be high molecular weight polymers. In some embodiments, the polymer nucleating agents may have the formula (I)-(V) as shown above, and a number average molecular weight greater than about 5000. In other embodiments, suitable polymeric nucleating agents may have the formula (I)-(V) as shown above, with y ranging from 8 to 30 and n being 7 or greater. Such high molecular weight polymers are not useful as phase change solvents because their phase change temperatures may be near or higher than the processing temperature such that they remain solid at the processing temperature. In some embodiments, the polymeric nucleating agents are present in an amount from about 0.1 to about 50 wt %, preferably from about 1 to about 30 wt %, and more preferably from about 3 to about 15 wt %.

Even in the absence of those optional nucleating agents disclosed above, the phase change solvents may exhibit a "self-nucleating" behavior. That is, upon cooling, higher molecular weight phase change solvent molecules crystallize or solidify first, and serve as nuclei for lower molecular weight phase change solvent molecules.

Optionally, various thermoplastic polymers may be used in the present compositions in an amount from about 1 to about 50 wt %, preferably from about 5 to about 40 wt %, and more preferably from about 10 to about 30 wt %. Suitable thermoplastic polymers may associate with the hard blocks of the block copolymers to form an entangled three-dimensional network. Thermoplastic polymers such as polyphenylene oxide, and alkenylarene resins derived from monomers including styrene, α-methyl styrene, other styrene derivatives, vinyl toluene, and mixtures thereof, are useful in the present invention. These polymers are suitable because they are chemically compatible with the styrenic hard blocks of the block copolymer. Not intending to be bound by theory, it is believed to be advantageous to have compatible components in a composition so that the components may be intimately mixed to form an entangled three-dimensional network structure. This entangled network structure is believed to be capable of improving the mechanical properties, such as tensile, elastic and stress relaxation properties.

Other additives may be incorporated into the present compositions include stabilizers and/or anti-oxidants, dyes, pigments, fillers, anti-blocking agents, flame retardants, and the like.

The shear viscosity of the compositions, measured at 175° C. and 1 $sec^{-1}$ shear rate, may be from about 0.1 Pa-s to about 3,000 Pa-s. Because the compositions of the present invention provide a broad range of viscosities, they are processable by a wide variety of processes. In some embodiments useful for printing or spraying, the compositions of the present invention may have shear viscosities ranging from about 1 to about 150 Pa s, preferably from about 5 to about 100 Pa s, and more preferably from about 10 to about 80 Pa·s, at 175° C. and 1 $s^{-1}$ shear rate.

Figure 2:
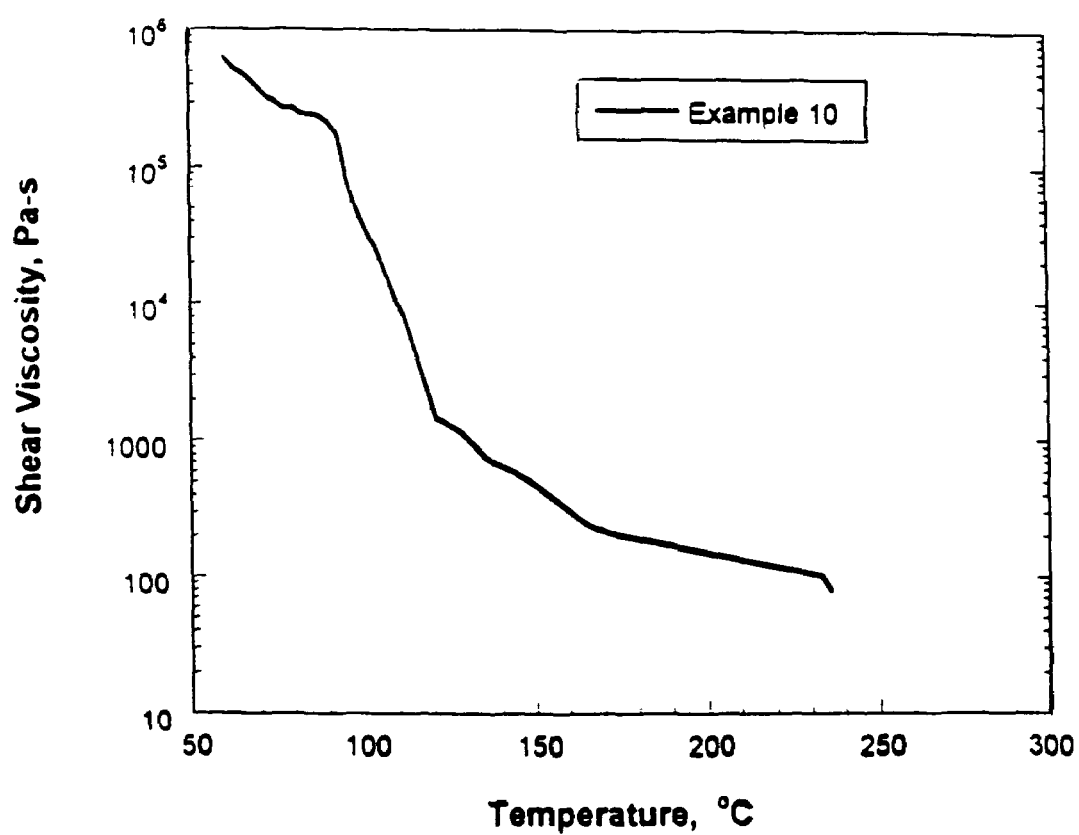
FIG. 2 is a shear viscosity/temperature curve of a composition of the present invention.

FIG. 2 shows the shear viscosity/temperature curve of the elastomeric composition of Example 10. The elastomeric composition of Example 10 comprises the phase change solvent of Example 1, a styrenic TPE and a processing oil. As shown in FIG. 1, the phase change temperature of Example 1 is at or below about 100° C. As shown in FIG. 2, below change the phase change temperature of the phase change solvent, the composition is substantially solid-like and the shear viscosity increases exponentially. However, the composition exhibits an immediate and significant drop in shear viscosity around the phase change temperature.

Figure 3:
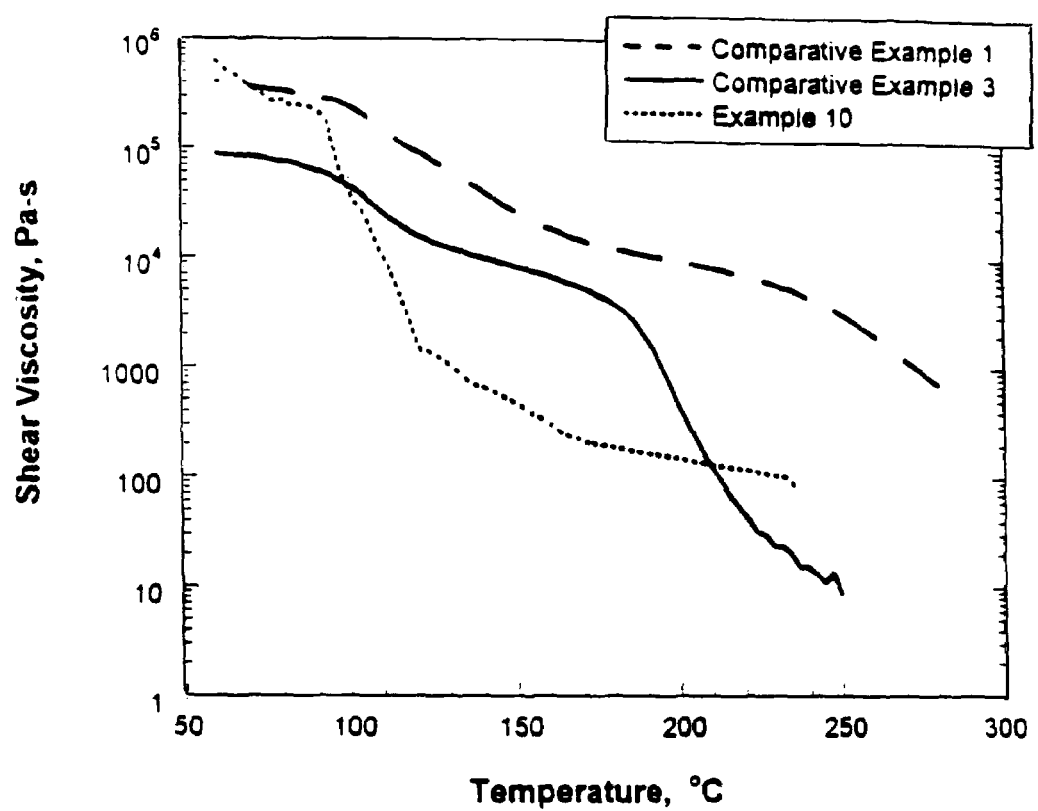
FIG. 3 is a comparison between shear viscosity/temperature curves of previously known compositions and that of a composition of the present invention.

FIG. 3 compares the shear viscosity/temperature curve of Example 10 and of previously known elastomeric compositions of Comparative Examples 1 and 3. These comparative compositions comprise polystyrene, a styrenic TPE and a processing oil. Comparative Example 1 exhibits only a gradual viscosity decrease with temperature. Even at a fairly high temperature of 250° C., the shear viscosity remains about 3000 Pa s. Comparative Example 3 exhibits a significant decrease in shear viscosity at or above 200° C. As such, the Comparative Examples require relatively high processing temperature and may not be suitable for certain processes or applications that use low processing temperatures, low thermally stable substrates or structurally delicate substrates. In contrast, Example 1 exhibits a significant decrease in shear viscosity at a much lower temperature, thus, the composition of the present invention is more processable for various processes and applications.

Since the phase change solvents may lower the shear viscosity of the compositions of the present invention, some embodiments of the present invention may be processed at a temperature at least about 10° C., preferably at least about 30° C. and more preferably at least 50° C. higher than the phase change temperature of the phase change solvent in the composition. Thus, the processing temperature for some embodiments of the present invention may be processed at a temperature at least about 50° C., preferably at least about 70° C., more preferably at least about 100° C. and most preferably at least about 120° C.

In one embodiment, the composition of the present invention may have a normalized peak load of from about 100 to about 1000 Newtons/meter (N/m), preferably from about 200 to about 800 N/m, and more preferably from about 300 to about 700 N/m. In another embodiments, the composition of the present invention may have a peak strain of at least about 200%, preferably at least about 300%, and more preferably at least about 400%. In another embodiment, the composition of the present invention may have a room temperature normalized load at 200% strain of from about 40 to about 250 N/m, preferably from about 50 to about 200 N/m, and more preferably from about 60 to about 150 N/m. In another embodiment, the composition of the present invention may also have a force relaxation at 200% strain of less than about 50%, more preferably less than about 35%, and most preferably less than about 20%, at room temperature and 30 seconds hold time.

The compositions of the present invention are suitable for use in elastic components of disposable articles, such as taped or fastened diapers, training pants, pull-on diapers, adult incontinence products, bandages, wraps, wound dressings, surgical drapes, and the like. The elastic components may be portions of the absorbent article, such as the waistbands, leg cuffs, side panels, stretch ears, topsheet, and outer cover, that provide a body-conforming function, a restraint function, or other functions of the disposable article when it is worn. The compositions may also be used as stretchable woven or nonwoven fabric in durable articles, stretch garments including sports wear, swimwear, socks, undergarments, medical garments or devices, and the like.

TEST METHODS

A. Differential Scanning Calorimetry (DSC)

DSC is a well known method for thermal measurements. This method is capable of determining the temperature ranges at which the phase changes of materials occur. Here, the phase change temperatures are useful in selecting the phase change solvents and correlating with the processability and mechanical properties of the elastomeric compositions containing them.

The measurements were performed using a Model 822 DSC from Mettler, Columbus, Ohio or a System 7 DSC from Perkin-Elmer, Shelton, Conn. The instrument is interfaced with a computer for controlling the heating/cooling rates and other test parameters, and for collecting, calculating and reporting the data. The test procedure follows that of ASTM D3418 generally. The procedure is as follows:

(1) calibrate the instrument according to the manufacture's instructions;

(2) a sample material (ca. 15 mg) is placed into aluminum pans, capped, crimped and placed into the instrument according to manufacturer's instructions;

(3) if testing a new material, it may be necessary to perform one or more trial scans to determine an appropriate temperature range for the measurements, which should provide sufficient baseline before and after the observed transition; a typical temperature scan ranges from −50° C. to about 50° C. above the highest phase transition temperature of the sample being tested; for the phase change solvents of the present invention, a typical DSC scan ranges from −50° C. to 200° C.;

(4) program the instrument as follows: the sample temperature is set to the lower limit of desired test range; the temperature is held at the lower limit for 5 minutes and then it is increased at a rate of 10° C./min until reaching the upper limit; the temperature is held at the upper limit for 5 minutes and then the sample is cooled to the lower limit at 10° C./min; the temperature is held at the lower limit for 5 minutes and then the sample is heated at 10° C./min to the upper limit for a second heating scan;

(5) start the test and collect data simultaneously;

The results (including onset temperature, the peak temperature, the heat of phase transition) from the second heating scan are reported.

B. Pre-Strained Tensile Test

The properties determined by this method may correlate with the elastic forces a wearer feels from an elastic component incorporated into an absorbent product. The pre-straining step simulates the condition the elastic component experiences as the product is initially stretched in order to put the product on a wearer or to adjust the product to fit the wearer.

A commercial tensile tester from Instron Engineering Corp., Canton, Mass. or SINTECH-MTS Systems Corporation, Eden Prairie, Minn. may be used for this test. The instrument is interfaced with a computer for controlling the test speed and other test parameters, and for collecting, calculating and reporting the data.

The sample is prepared by placing about 2 grams of the composition, which has been homogenized in chloroform and dried, between two TEFLON® sheets and this assembly is placed in a Carver Press. Metal shims with a thickness of 0.2 mm (10 mils) are placed between the TEFLON® sheets to control the thickness of the pressed film. The press is allowed to heat up to 175° C., then a 700 pounds (1540 kg) of pressure is applied for 5-10 seconds. The pressed film is immediately removed from the press and placed between two aluminum blocks (1" or 25.4 mm thick) to cool the film rapidly. The test samples (1" or 25.4 mm wide by 2" or 50.8 mm long) are cut from the pressed film. All surfaces of the sample shall be free of visible flaws, scratches or imperfections.

This test is done under standard laboratory conditions (i.e., at about 25° C. and about 50% relative humidity. The procedure is as follows:

(1) choose appropriate jaws and load cell for the test; the jaws should be wide enough to fit the sample, typically 1" wide jaws are used; the load cells is chosen so that the response from the sample tested will be between 25% and 75% of the capacity of the load cells or the load range used, typically a 50 lb load cell is used;

(2) calibrate the instrument according to the manufacture's instructions;

(3) set the gauge length at 1" (25.4 mm), and place the sample in the instrument according to the manufacture's instructions;

(4) stretch the sample at a constant speed of 10"/min (0.254 m/min) until it reaches 500% strain i.e., the gauge length is now 6" (15.24 cm); then return to the original gauge length at 10"/min (0.254 m/min); and at the end of this pre-straining cycle, start timing the experiment using a stop watch;

(5) reclamp the pre-strained sample to remove any slack and still maintain a 1" (25.4 mm) gauge length;

(6) at the three minute mark on the stop watch, start stretching the sample at a constant speed of 10"/min (0.254 m/min); the instrument records the forces versus time during this cycle;

(7) the result is plotted as a force versus time curves; the peak load and the peak strain can be obtained from the plot. The peak load is normalized and reported. The average result of three samples is reported. For this test, the peak load is normalized to 85 gsm as follows: the peak load from the plot is divided by the width of the sample, then multiplied by a normalizing factor, which is 85/(½*(actual weight of the sample/(width*gauge length) of sample in m$^2$)), or 85/(½(actual weight of the sample)/(6.47×10$^{-4}$)) if the sample dimension is measured in inches.

C. Force or Stress Relaxation Test

The property determined by this method may correlate with the forces a wearer experiences from an elastic component incorporated into a product. The first cycle is a pre-straining step that simulates the conditions the elastic component experiences as the product is initially stretched in order to put the product on a wearer or to adjust the product to fit the wearer. The second cycle measures the reduction in elastic forces (i.e., stress relaxation) resulting from the pre-straining step.

The instrument, the sample preparation and the laboratory conditions are the same as Test Method A above. The procedure is as follows:

(1) choose appropriate jaws and load cell for the test; the jaws should be wide enough to fit the sample, typically 1"(25.4 mm) wide jaws are used; the load cells is chosen so that the response from the sample tested will be between 25% and 75% of the capacity of the load cells or the load range used, typically a 50 lb (22.7 kg) load cell is used;

(2) calibrate the instrument according to the manufacturer's instructions;

(3) set the gauge length at 1" (25.4 mm) and place the sample in the instrument according to the manufacturer's instructions;

(4) set the cross head speed at a constant speed of 10"/min (0.254 m/min);

(5) Prestrain the sample to 500% strain and immediately (i.e., without holding time) return to 0% strain;

(6) Reclamp the prestrained sample to remove any slack and maintain a 1" (2.54 cm) gauge length;

(7) Start the sustained load stress relaxation test and collect data simultaneously, the sustained load stress relaxation test has the following steps:

a) go to 200% strain at a rate of 10"/min (0.254 m/min);
b) hold position for 30 seconds;
c) go to 0% strain at the at a of 10"/min (0.254 m/min); and
d) calculate the stress relaxation at 200% strain as the % loss between the initial load and the load at time t of step 7(b) as follows:

$$\% \text{ Force Relaxation at time, } t = \frac{[(\text{initial load}) - (\text{load at time, } t)]}{(\text{initial load})} \times 100$$

(8) The average result of three samples is reported. The load at 200% strain of step 7(a) is normalized to 85 gsm as follows: the load at 200% strain from the plot is divided by the width of the sample, then multiplied by a normalizing factor, which is 85/(½*(actual weight of the sample/(width*gauge length) of sample in m$^2$)), or 85/(½*(actual weight of the sample)/(6.47×10$^{-4}$)) if the sample dimension is measured in inches.

D. Molecular Weight Determination

Number-average molecular weights are estimated by analysis of the NMR (Nuclear Magnetic Resonance) spectra of the compounds. Methyl end groups are quantified via their peak at 1 ppm while the aromatic content is quantified by their peak at approximately 7-8 ppm. Methylene esters are quantified via their peak at approximately 4-4.5 ppm and aliphatic methylenes are quantified via their peaks from 1.5-2.5 ppm. From these quantified values a product structure is determined and the molecular weight is calculated.

E. Shear Viscosity Test

Samples are prepared by the hot press method described in Test Method B, except that about 5 grams of homogenized composition and 1.2 mm (60 mils) thick metal shims are used.

Shear viscosity of the sample can be measured using the ARES Polymer Melt Rheometer (manufactured by Rheometrics, Piscataway, N.J.) in the parallel plate mode. The sample handling and instrument operation generally follow the operating manual provided by the manufacturer, except for the specific testing conditions described herein. In this test, parallel plates that are 25 mm in diameter and have 1 mm gap between them are used and the instrument is equipped with a heated chamber to control the test temperature.

The hot pressed sample is loaded into the instrument, which is preheated to a temperature of about 100° C. Then the parallel plates are pressed together leaving a gap distance of 1 mm between them. After a sufficient time to allow the sample to equilibrate, excess sample is removed. Depending on the material, the shear viscosity is either measured in steady or dynamic mode with the rheometer. In steady mode, the instrument performs a rate sweep, wherein the shear rate is ramped up from 0.1 s$^{-1}$ to 100 s$^{-1}$ and viscosity($\square$ measurements are taken at regular intervals (typically 5 points per decade of shear rate).

In dynamic mode, the complex shear viscosity $\square$* is measured at 1 s$^{-1}$ oscillating at 5% strain. The instrument is operated in a temperature scan mode, wherein the temperature is ramped up at 5° C./min over the range from 100° C. to at least 50° C. above the highest phase transition temperature. Some samples may require higher loading temperature in order to fill the gap between the parallel plates. The loading temperature may be adjusted higher as needed and the temperature scan will start at the higher temperature.

EXAMPLES

Example 1

A phase change solvent having the general structure (I) is prepared by combining 260 grams (2 moles) of octanol with 404 grams (2 moles) of terephthaloyl chloride and 202 grams (1 mole) of 1,12-dodecanediol in 1500 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting reaction mixture is poured into a large quantity of methanol to precipitate the product. The precipitant is collected over a filter, washed with 500 ml of methnaol 3 times and dried at 45° C. in an vacuum oven for 20 hours. The resulting product has a number-average molecular weight of about 720 and an AA ratio of 2.3.

Example 2

A phase change solvent having the general formula (I) is prepared by combining 260 grams (2 moles) of octanol with 502 grams (2 moles) of naphthalene-dicarboxylic acid chloride and 146 grams (1 mole) of 1,8-octanediol in 1500 ml of chloroform in a reaction flask. The reaction conditions and the product collection steps are the same as in Example 1. The resulting product has a number-average molecular weight of about 770 and an AA ratio of 1.2.

Example 3

A phase change solvent having the general formula (II) is prepared by combining 130 grams (1 moles) of octanol with 404 grams (2 moles) of terephthaloyl chloride and 404 grams (2 mole) of 1,12-dodecanediol in 1200 ml of chloroform in a reaction flask. The reaction conditions and the product collection steps are the same as in Example 1. The resulting product has a number-average molecular weight of about 790 and an AA ratio of 2.7.

Example 4

A phase change solvent having the general formula (III) is prepared by combining 130 grams (1 moles) of octanol with 404 grams (2 moles) of terephthaloyl chloride in 250 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting product is concentrated via vacuum distillation at the boiling point of chloroform followed by dilution with 250 ml of acetone and 2 ml of water. After stirring for 4 hours, the solution is filtered and concentrated by vacuum distillation at the boiling point of acetone and the product is dried at 45° C. under vacuum for 20 hours. The resulting product has a number-average molecular weight of about 280 and an AA of 1.3.

Example 5

A phase change solvent having the general formula (I) is prepared by combining 260 grams (2 moles) of octanol with 502 grams (2 moles) of naphthalene-dicarboxylic acid chloride and 202 grams (1 mole) of 1,12-dodecanediol in 1500 ml of chloroform in a reaction flask. The reaction conditions and the product collection steps are the same as in Example 1. The resulting product has a number-average molecular weight of about 820 and an AA ratio of 1.4.

Example 6

A phase change solvent having the general formula (II) is prepared by combining 161 grams (1 moles) of octanol with 404 grams (2 mole) of 1,12-dodecanediol in 1000 ml tetrahydrofuran and 195 grams (5 moles) of potassium in a reaction flask. After stirring for 24 hours, 346 grams (2 moles) of 1,4-dichloroxylene is added to the mixture. The mixture is allowed to react at 55° C. for 20 hours with constant stirring. The reaction is terminated by cooling the mixture to room temperature. The resulting mixture is poured into a large quantity of methanol to precipitate the product. The precipitant is collected over a filter, washed with 500 ml of methnaol 3 times, and dried at 45° C. under vacuum for 20 hours. The resulting product has a number-average molecular weight of about 720 and an AA ratio of 2.7.

Example 7

A phase change solvent having the general formula (III) is prepared by combining 162.5 grams (1 moles) of octanoyl chloride with 220 grams (2 moles) of hydroquinone in 400 ml of chloroform in a reaction flask. The mixture is allowed to react at 55° C. for 20 hours with constant stirring and under a vacuum, which removes HCl generated by the reaction. The reaction is terminated by cooling to room temperature. The resulting product is concentrated via vacuum distillation at the boiling point of chloroform followed by dilution with 250 ml of acetone and 2 ml of water. After stirring for 4 hours, the mixture is filtered and concentrated by vacuum distillation at the boiling point of acetone and the product is dried at 45° C. under vacuum for 20 hours. The precipitant is collected over a filter, washed with 500 ml of methanol 3 times and dried at 45° C. under vacuum for 20 hours. The resulting product has a number-average molecular weight of about 240 and an AA of 1.3.

Example 8

A phase change solvent having the general formula (I) is prepared by combining 260 grams (2 moles) of octanol with 202 grams (1 moles) of terephthaloyl chloride in 400 ml of chloroform in a reaction flask. The mixture is allowed to react at 55° C. for 20 hours with constant stirring and under a vacuum, which removes HCl generated by the reaction. The reaction is terminated by cooling the mixture to room temperature. The resulting product is collected by pouring the mixture into a large quantity of cold methanol (0° C.) to precipitate the product. The precipitant is collected over a filter, washed with 500 ml of cold methanol (at 0° C.) 3 times and dried at 25° C. under vacuum for 20 hours. The resulting product has a number-average molecular weight of about 390 and an AA ratio of 2.7.

Examples 9-20

An elastomeric composition is prepared by mixing and stirring the phase change solvent of Example 1 and SEPTON® S4033 (available from Kuraray America, Inc., New York, N.Y.) at 120° C. for 4 hours or until the sample appears to be homogeneous. The mixture is cooled to room temperature. Mineral oil, DRAKEOL® Supreme (available from Pennzoil Co., Penrenco Div., Karns City, Pa.) is then added to the mixture and stirred at room temperature for 16 hours to form an elastomeric composition.

Alternative, the composition is prepared by mixing all the components in chloroform (5 grams total weight of the composition in 45 grams of chloroform) and stirring for 2 hours or until the mixture appears homogeneous. The mixture is then poured into a TEFLON® dish and let dry at room temperature overnight. The mixture and the TEFLON® dish are placed in a vacuum oven for an hour at 60° C.

The above blending method is merely exemplary. Other conventional blending methods using batch mixers, screw extruders, and the like, may also be used.

Comparative Examples 1-2

Elastomeric compositions (comparative examples 1-2) are prepared with SEPTON® S4033 (from Kuraray America, Inc. New York, N.Y.), polystyrene NOVACOR® PS 3900 (from Nova Chemicals, Inc., Monaca, Pa.), and mineral oil, DRAKEOL® Supreme (from Pennzoil Co., Penrenco Div., Karns City, Pa.). Elastomeric compositions are also prepared with VECTOR® 4211 (available from Dexco Chemical Company, Houston, Tex.), instead of SEPTON®. The compositions may be prepared by any of the methods described above. The components (shown in weight percent) for the comparative examples and their properties, in comparison with exemplary compositions of the present invention are listed in Tables 1 and 2.

TABLE 1

| Example | Comp. 1 | Comp. 2 | 9 | 10 | 11 | 12 | 13 | 14 | 15 |
|---|---|---|---|---|---|---|---|---|---|
| SEPTON® S-4033 | 50 | 40 | 50 | 50 | 50 | 40 | 40 | 50 | 40 |
| Polystyrene | 20 | 30 | | | | | | | |
| Mineral oil | 30 | 30 | 30 | 25 | 20 | 40 | 30 | 20 | 30 |
| Example 1 (C8-C12)* | | | 20 | 25 | 30 | 20 | 30 | | |
| Example 2 (C8-C8)** | | | | | | | | 30 | 30 |
| $\eta^*$ @ 175° C., 1 s$^{-1}$ steady (Pa-s) | 5770 | 3209 | 429 | 237 | 89 | 51 | 24 | 32 | 37 |
| Norm.^ Peak Load (N/m) | 501 | 460 | 612 | 642 | 513 | 360 | 308 | 341 | 133 |
| Peak Strain (%) | 506 | 870 | 705 | 621 | 550 | 680 | 580 | 490 | 486 |
| Norm.^ Load @ 200% strain (N/m) | 118 | 154 | 88 | 96 | 126 | 63 | 78 | 123 | 78 |
| % Force Relaxation @ 200% strain, RT, 30 sec | 12 | 17 | 10 | 11 | 15 | 10 | 12 | 14 | 12 |

*(C8-C12) represents a phase change solvent of formula (I) having R, R' = H, y = 8, x = 12 and n = 2.
**(C8-C8) represents a phase change solvent of formula (I) having R, R' = H, y = 8, x = 8 and n = 2.
^ Normalized to 85 gsm The above examples show that, with respect to Comparative Examples 1-2, the incorporation of a phase change solvent significant decreases shear viscosity and provides satisfactory elastic and tensile properties. Examples 9-15 further show that the phase change solvent is more effective than mineral oil in lowering the shear viscosity of the elastomeric composition without substantially compromising or even improve the elastic and tensile properties.

TABLE 2

| Example | Comp. 3 | Comp. 4 | 16 | 17 | 18 | 19 | 20 |
|---|---|---|---|---|---|---|---|
| VECTOR® 4211 | 50 | 70 | 50 | 50 | 50 | 70 | 70 |
| Polystyrene | 20 | 10 | | 10 | 10 | | |
| Mineral oil | 30 | 20 | 30 | 20 | 20 | 20 | 20 |
| Example 1 (C8-C12)* | | | 20 | 20 | | 10 | |
| Example 2 (C8-C8)** | | | | | 20 | | 10 |
| $\eta^*$ @ 175° C., 1 s$^{-1}$ steady (Pa-s) | 4945 | 3911 | 11 | 70 | 163 | 1061 | 1440 |
| Norm.^ Peak Load (N/m) | 61 | 377 | 54 | 391 | 232 | 271 | 302 |
| Peak Strain (%) | 322 | 834 | 348 | 856 | 653 | 1027 | 1210 |
| Norm.^ Load @ 200% strain (N/m) | 31 | 79 | 38 | 53 | 59 | 71 | 60 |
| % Force Relaxation @ 200% strain, RT, 30 sec | 8 | 11 | 10 | 12 | 11 | 9 | 9 |

*(C8-C12) represents a phase change solvent of formula (I) having R, R' = H, y = 8, x = 12 and n = 2.
**(C8-C8) represents a phase change solvent of formula (I) having R, R' = H, y = 8, x = 8 and n = 2.
^ Normalized to 85 gsm The above examples show even for compositions which comprise a relatively melt flowable and more processable styrenic TPE (such as VECTOR®), the incorporation of a phase change solvent is still effective in lowering the shear viscosity without substantially compromising the tensile and elastic properties.

All documents cited in the Detailed Description of the Invention are, in relevant part, incorporated herein by reference; the citation of any document is not to be construed as an admission that it is prior art with respect to the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A composition comprising:
   a) from about 1 to about 99 wt % a thermoplastic elastomer, which is a block copolymer having at least one soft block and at least one hard block;
   b) from about 1 to about 70 wt % a phase change solvent having the general formula:

$$R'—P_y\text{-}(Q\text{-}P_x)_{n-2}\text{-}Q\text{-}P_y—R; \quad (I)$$

$$R'—P_y\text{-}(Q\text{-}P_x)_n—R; \quad (II)$$

$$R'\text{-}(Q\text{-}P_x)_n—R; \quad (III)$$

$$R'\text{-}(Q\text{-}P_x)_{n-1}\text{-}Q\text{-}P_y—R; \quad (IV)$$

$$R'\text{-}(Q\text{-}P_x)_{n-1}\text{-}Q\text{-}R; \text{ or} \quad (V)$$

mixtures thereof; (VI)

wherein Q is a para-ring substituted difunctional aromatic moiety, and wherein the substitutions are in the 1,4 positions; P is $CH_2$; R and R' are the same or different and are independently selected from H, $CH_3$, COOH, $CONHR_1$, $CONR_1R_2$, $NHR_3$, $NR_3R_4$, hydroxyl, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 3 to 7;
   wherein the phase change solvent has a phase change in a temperature range from about 40° C. to about 250° C.

2. The composition of claim 1 wherein the phase change solvent exhibits at least one phase change which is a crystalline transition, a glass transition, or a liquid crystalline transition.

3. The composition of claim 1 wherein the phase change solvent has a number-average molecular weight from about 150 to about 5,000.

4. The composition of claim 1 wherein Q comprises one or more substituents on the aromatic ring and the substituent is selected from H, C1-C30 alkyl, COOH, $CONHR_5$, $CONR_5R_6$, $NHR_7$, $NR_7R_8$, hydroxyl, C1-C30 alkoxy, $SO_3H$, or halogen; wherein $R_5$, $R_6$, $R_7$ and $R_8$ are the same or different and are independently selected from H or linear or branched alkyl from C1-C30.

5. The composition of claim 1 wherein the alkenylarene polymer block is derived from monomers selected from the group consisting of styrene, α-methyl styrene, vinyl toluene, and mixtures thereof; and the olefin polymer block is derived from monomers selected from the group consisting of ethylene, propylene, butadiene, isoprene, and mixtures thereof.

6. The composition of claim 1 wherein the block copolymer is a styrene-olefin-styrene triblock copolymer selected from the group consisting of styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-IB-S) and mixtures thereof.

7. The composition of claim 3 further comprising a nucleating agent having the formula:

$$R'—P_y\text{-}(Q\text{-}P_x)_{n-1}\text{-}Q\text{-}P_y—R; \quad (I)$$

$$R'—P_y\text{-}(Q\text{-}P_x)_n—R; \quad (II)$$

$$R'\text{-}(Q\text{-}P_x)_n—R; \quad (III)$$

$$R'\text{-}(Q\text{-}P_x)_{n-1}\text{-}Q\text{-}P_y—R; \text{ or} \quad (IV)$$

$$R'\text{-}(Q\text{-}P_x)_{n-1}\text{-}Q\text{-}R; \quad (V)$$

and a number average molecular weight greater than about 5000; wherein Q is a para-ring substituted difunctional aromatic moiety, and wherein the substitutions are in the 1,4 positions; P is $CH_2$; R and R' are the same or different and are independently selected from H, $CH_3$, COOH, $CONHR_1$, $CONR_1R_2$, $NHR_3$, $NR_3R_4$, hydroxyl, or C1-C30 alkoxy; wherein $R_1$, $R_2$, $R_3$ and $R_4$ are the same or different and are independently selected from H or linear or branched alkyl from C1-C30; x is an integer from 1 to 30; y is an integer from 1 to 30; and n is an integer from 3 to 7.

8. The composition of claim 1 wherein the processing oil is mineral oil, paraffinic oil, naphthenic oil, petrolatum, waxes, olefinic oligomers, or mixtures thereof.

9. The composition of claim 1 wherein the thermoplastic polymer is selected from the group consisting of polystyrene, poly(α-methyl styrene), polyphenylene oxide, polyolefins, and mixtures thereof.

10. The composition of claim 1 wherein the composition has a shear viscosity of about 0.1 to about 3000 Pa·s at 175° C. and 1 $sec^{-1}$.

11. A method of lowering the viscosity and improving the processability of a thermoplastic elastomer, the method comprising the step of: blending from about 1 to about 99 wt % of the thermoplastic elastomer, which is a block copolymer having at least one soft block and at least one hard block, and from about 1 to about 70 wt % of a phase change solvent having the general formula (I)-(V) of claim 1, or a mixture thereof, to form an elastomeric composition; wherein Q of the general formula (I)-(V) of claim 1 is a para-ring substituted difunctional aromatic moiety, and wherein the substitutions are in the 1,4 positions, and wherein the shear viscosity of the elastomeric composition is lower than the shear viscosity of the thermoplastic elastomer when measured at 175° C. and 1 $sec^{-1}$; and further wherein the phase change solvent has a phase change temperature range from about 40° C. to about 250° C.

12. The method of claim 11 wherein the elastomeric composition has a shear viscosity of about 0.1 to about 3000 Pa·s at 175° C. and 1 $sec^{-1}$.

13. The method of claim 11 further comprising blending one or more additional ingredient with the thermoplastic elastomer and the phase change solvent, wherein the additional ingredient is selected from the group consisting of:
   from about 1 to about 70 wt % of a processing oil;
   from about 0.1 to about 50 wt % of a nucleating agent;
   from about 1 to about 50 wt % of a thermoplastic polymer; and
   mixtures thereof.

14. The composition of claim 1 further comprising from about 1 to about 70 wt % of a processing oil.

15. The composition of claim 1 further comprising from about 0.1 to about 50 wt % of a nucleating agent.

16. The composition of claim 15 wherein said nucleating agent is a particulate material selected from the group consisting of talc, silica, carbon black, clay, metal oxides, metal carbonates, and mixtures thereof.

17. The composition of claim 1 further comprising from about 1 to about 50 wt % of a thermoplastic polymer.

18. The composition of claim 1 wherein an AA ratio ($C_{aliphatic}$ to $C_{aromatic}$) of said phase change solvent ranges from about 0.25 to about 4.

19. The composition of claim 1 wherein said composition is incorporated into one or more components of a fastenable diaper, a training pant, a pull-on diaper, and an adult incontinence product.

20. The composition of claim 1 wherein said composition is incorporated into a diaper component selected from the group consisting of waistbands, leg cuffs, side panels, stretch ears, topsheet, outer covers, and combinations thereof.

21. The composition of claim 1 wherein said composition has a normalized peak load of from about 100 to about 1000 Newtons/meter (N/m).

22. The composition of claim 1 wherein said composition has a peak strain of at least about 200%.

23. The composition of claim 1 wherein said composition has a room temperature normalized load at 200% strain of from about 40 to about 250 N/m.

24. The composition of claim 1 wherein said composition has a force relaxation at 200% strain of less than about 50%.

* * * * *

UNITED STATES PATENT AND TRADEMARK OFFICE
CERTIFICATE OF CORRECTION

PATENT NO. : 7,459,494 B2  
APPLICATION NO. : 10/429432  
DATED : December 2, 2008  
INVENTOR(S) : Mark William Hamersky et al.

It is certified that error appears in the above-identified patent and that said Letters Patent is hereby corrected as shown below:

<u>Column 8</u>

Lines 64-65, delete "polystyrene-isoprenelbutadiene-styrene" and insert

-- polystyrene-isoprene/butadiene-styrene --.

Signed and Sealed this

Eleventh Day of August, 2009

David J. Kappos  
*Director of the United States Patent and Trademark Office*